United States Patent [19]

Holmwood et al.

[11] Patent Number: 4,960,456

[45] Date of Patent: Oct. 2, 1990

[54] FUNGICIDAL AND PLANT GROWTH-REGULATING NOVEL SUBSTITUTED 1-HYDROXYALKYL-AZOLYL DERIVATIVES

[75] Inventors: Graham Holmwood; Erik Regel, both of Wuppertal; Gerhard Jäger, Leverkusen; Karl H. Büchel, Burscheid; Klaus Lürssen, Bergisch Gladbach; Paul-Ernst Frohberger, Leverkusen; Wilhelm Brandes, Leichlingen; Volker Paul, Solingen, all of Fed. Rep. of Germany

[73] Assignee: Bayer Aktiengesellschaft, Leverkusen, Fed. Rep. of Germany

[21] Appl. No.: 354,329

[22] Filed: May 19, 1989

Related U.S. Application Data

[60] Division of Ser. No. 121,552, Nov. 17, 1987, Pat. No. 4,904,296, which is a division of Ser. No. 683,891, Dec. 20, 1984, Pat. No. 4,734,126, which is a continuation of Ser. No. 458,086, Jan. 14, 1983, abandoned.

[30] Foreign Application Priority Data

Jan. 27, 1982 [DE] Fed. Rep. of Germany ....... 3202601

[51] Int. Cl.$^5$ .................. A01N 43/653; C07D 249/08
[52] U.S. Cl. ........................................ 71/92; 71/76; 548/101; 548/267.8; 548/268.6; 514/184; 514/383
[58] Field of Search ...................... 71/92, 76; 548/101, 548/262; 514/184, 383

[56] References Cited

U.S. PATENT DOCUMENTS

| | | | |
|---|---|---|---|
| 4,243,405 | 1/1981 | Sugavanam et al. | 548/262 |
| 4,255,434 | 3/1981 | Kramer et al. | 548/262 |
| 4,406,909 | 9/1983 | Kramer et al. | 548/341 |
| 4,414,210 | 11/1983 | Miller et al. | 548/262 |
| 4,507,140 | 3/1985 | Sugavanam | 71/92 |
| 4,549,900 | 10/1985 | Kramer et al. | 548/262 |
| 4,723,984 | 2/1988 | Holmwood et al. | 548/262 |

FOREIGN PATENT DOCUMENTS

| | | | |
|---|---|---|---|
| 0040345 | 11/1981 | European Pat. Off. | 548/262 |
| 0052424 | 5/1982 | European Pat. Off. | 548/262 |
| 0057357 | 8/1982 | European Pat. Off. | 514/383 |
| 0061051 | 9/1982 | European Pat. Off. | 514/383 |
| 0061835 | 10/1982 | European Pat. Off. | 548/262 |
| 3018865 | 11/1981 | Fed. Rep. of Germany | 548/262 |

*Primary Examiner*—Glennon H. Hollrah
*Assistant Examiner*—Patricia L. Morris
*Attorney, Agent, or Firm*—Sprung Horn Kramer & Woods

[57] ABSTRACT

Compounds which are substituted 1-hydroxyalkyl-azolyl derivatives of the general formula

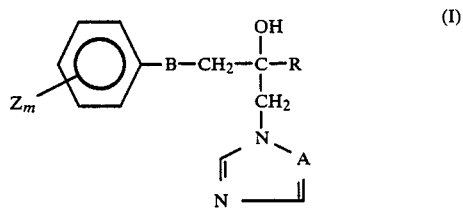

in which
A represents a nitrogen atom or a CH group,
B represents oxygen, sulphur or a CH$_2$ group,
R represents a substituted alkyl, and, in the case in which B represents sulphur, also represents an unsubstituted alkyl, optionally substituted cyclo-alkyl or optionally substituted phenyl group,
Z represents a halogen atom or an alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenylalkoxy group, and
m is 0, 1, 2 or 3, and the acid addition salts and metal salt complexes thereof, are new, are prepared as described and find use as fungicides and plant growth regulators.

6 Claims, No Drawings

FUNGICIDAL AND PLANT GROWTH-REGULATING NOVEL SUBSTITUTED 1-HYDROXYALKYL-AZOLYL DERIVATIVES

This is a division of application Ser. No. 121,552, filed Nov. 17, 1987, now U.S. Pat. No. 4,904,296, which is a division of Ser. No. 683,891, filed Dec. 20, 1984, now U.S. Pat. No. 4,734,126, which is a continuation of Ser. No. 458,086, filed Jan. 14, 1983, now abandoned.

The present invention relates to certain new substituted 1-hydroxyalkylazolyl derivatives, to several processes for their production, and to their use as fungicides and plant growth regulators.

It has already been disclosed that certain triazolylalkanones and -ols, such as 1-phenyl- or 1-(4-chlorophenyl)-or 1-(2,4-dichlorophenyl)-2-(1,2,4-triazol-1-yl)-ethan-1-ol and 2,2-dimethyl-4-(1,2,4-triazol-1-yl)-dodecan-3-one and ω-phenyl-ω-(1,2,4-triazol-1-yl)acetophenone, possess fungicidal properties (see U.S. Ser. No. 792,756, filed May 2, 1977, now pending). However, the activity of these compounds is not always completely satisfactory, in particular when low amounts and concentrations are used. Furthermore, ether derivatives of certain hydroxyalkylimidazoles are known from the patent literature (see U.S. Pat. Nos. 4,123,542 and 4,277,475), which derivatives have an action against fungi which are pathogenic to humans, and may be used as medicaments and, in addition, also as contraceptives (U.S. Pat. No. 4,277,475).

Furthermore, it is known that 1-(4-chlorophenoxy)-3,3-dimethyl-1-(1,2,4-triazol-1-yl)-butan-2-one possesses good fungicidal activity (see U.S. Pat. No. 3,912,752). However, the action of this compound in certain fields of indication, such as, in particular, in rice diseases, is not always adequate, in particular when low amounts are used.

Furthermore, it has already been disclosed that certain biphenylyl-hydroxyalkyl-triazolyl derivatives, such as 2-(biphenyl-4-yl)-1-phenyl-3-(1,2,4-triazol-1-yl)-propan-2-ol and 1-(biphenyl-4-yl)-1-(2-chloro- or fluorophenyl)-2-(1,2,4-triazol-1-yl)-ethan-1-ol, possess generally good fungicidal properties and, when appropriate amounts are used, also possess a plant growth-regulating action. However, the activity of these compounds is not always satisfactory, in particular when low amounts and concentrations are used.

The present invention now provides, as new compounds, the 1-hydroxyalkyl-azolyl derivatives of the general formula

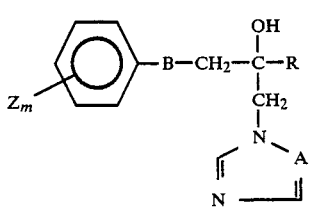

(I)

in which
A represents a nitrogen atom or a CH group,
B represents oxygen, sulphur or a $CH_2$ group,
R represents a substituted alkyl group, and, in the case in which B represents sulphur, also represents an unsubstituted alkyl, optionally substituted cycloalkyl or optionally substituted phenyl group,
Z represents a halogen atom or an alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenylalkoxy group, and
m is 0, 1, 2 or 3,
and the acid addition salts and metal salt complexes thereof.

The compounds of the formula (I) possess an asymmetric carbon atom, and may therefore be obtained in the forms of the two optical isomers.

The present invention further provides a process for the production of a compound of the present invention, characterized in that
(a) an oxirane of the general formula

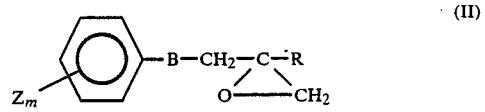

(II)

in which B, R, Z and m have the meanings given above, is reacted with an azole of the general formula

(III)

in which A has the meaning given above, in the presence of a diluent and, if appropriate, in the presence of a base, or
(b) an azolylmethyl-oxirane of the general formula

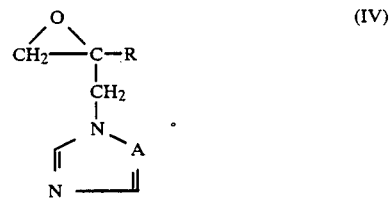

(IV)

in which A and R have the meanings given above, is reacted with a (thio)phenol of the general formula

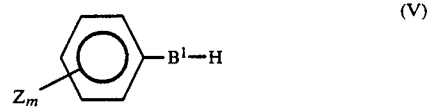

(V)

in which
Z and m have the meanings given above, and
$B^1$ represents oxygen or sulphur,
in the presence of a diluent and, if appropriate, in the presence of a base; and, if desired, an acid or a metal salt is then added onto the resulting compounds of the formula (I) obtained by reaction variant (a) or (b).

In addition, it has been found that the new substituted 1-hydroxyalkyl-azolyl derivatives of the formula (I) possess powerful fungicidal and powerful plant growth-regulating properties.

Surprisingly, the substituted 1-hydroxyalkyl-azolyl derivatives according to the invention, of the formula (I), exhibit better fungicidal and better plant growth-regulating actions than the abovementioned triazolyl derivatives known from the prior art. The active compounds according to the invention thus represent an enrichment of the art.

Preferred compounds of the present invention are those in which R represents a grouping of the general formula

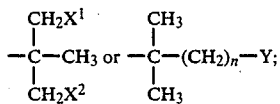

wherein
$X^1$ represents a hydrogen or halogen atom;
$X^2$ represents a halogen atom;
Y represents an alkyl, alkoxy, alkylthio, halogenoalkoxy, halogenoalkylthio, alkenyl having 2 to 6 carbon atoms, alkoxycarbonyl having 1 to 4 carbon atoms in the alkyl part or cyano group; or an optionally substituted radical selected from phenyl, phenoxy, phenylthio, phenylalkoxy having 1 to 4 carbon atoms in the alkyl part and phenylalkylthio having 1 to 4 carbon atoms in the alkyl part (the following being preferably mentioned as phenyl substituents in each case: halogen, alkyl having 1 to 4 carbon atoms; alkoxy and alkylthio, each having 1 or 2 carbon atoms; halogenoalkyl, halogenoalkoxy and halogenoalkylthio, each having 1 or 2 carbon atoms and 1 to 5 identical or different halogen atoms, such as, in particular, fluorine atoms and chlorine atoms, cyclohexyl, dialkylamino having 1 to 4 carbon atoms in each alkyl part, nitro, cyano, and alkoxycarbonyl having 1 to 4 carbon atoms in the alkyl part);
n is 0, 1 or 2;
Z represents a halogen atom, an alkyl group having 1 to 4 carbon atoms, a cycloalkyl group having 5 to 7 carbon atoms, an alkoxy or alkylthio group, each having 1 to 4 carbon atoms, a halogenoalkyl, halogenoalkoxy or halogenoalkylthio group, each having 1 or 2 carbon atoms and 1 to 5 identical or different halogen atoms, such as, in particular, fluorine atoms and chlorine atoms, or represents a phenyl, phenoxy or phenylalkyl or phenylalkoxy group having 1 or 2 carbon atoms in the alkyl part or in the alkoxy part, each of which is optionally substituted by halogen and alkyl having 1 or 2 carbon atoms; and
A, B and m have the abovementioned meanings.

Further preferred compounds of the present invention are those
in which
R represents a straight-chain or branched alkyl group having 1 to 4 carbon atoms, a cycloalkyl group which has 3 to 7 carbon atoms and is optionally substituted by alkyl having 1 or 2 carbon atoms, or an optionally substituted phenyl group (the following being mentioned as preferred substituents: halogen, alkyl having 1 to 4 carbon atoms and halogenoalkyl having 1 or 2 carbon atoms and 1 to 5 identical or different halogen atoms, such as, in particular, fluorine atoms and chlorine atoms);
B represents sulphur;
Z represents a halogen atom, an alkyl group having 1 to 4 carbon atoms, a cycloalkyl group having 5 to 7 carbon atoms, an alkoxy or alkylthio group, each having 1 to 4 carbon atoms, a halogenoalkyl, halogenoalkoxy or halogenoalkylthio group, each having 1 or 2 carbon atoms and 1 to 5 identical or different halogen atoms, such as, in particular, fluorine atoms and chlorine atoms, or represents a phenyl phenoxy, or phenylalkyl or phenylalkoxy group having 1 or 2 carbon atoms in the alkyl part or in the alkoxy part, each of which is optionally substituted by halogen and alkyl having 1 or 2 carbon atoms; and
A and m have the abovementioned meanings.

Particularly preferred compounds according to the present invention are those in which R represents a grouping of the general formula

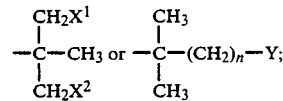

wherein
$X^1$ represents a hydrogen, fluorine, chlorine or bromine atom,
$X^2$ represents a fluorine, chlorine or bromine atom;
Y represents a methyl, ethyl, propyl, methoxy, ethoxy, methylthio, ethylthio, trifluoromethoxy, trifluoromethylthio, vinyl, methoxycarbonyl, ethoxycarbonyl or cyano group or an optionally substituted phenyl, phenoxy, phenylthio, phenylmethoxy or phenylmethylthio group (the phenyl substituent(s) in each case being selected from: fluorine, chlorine, methyl, ethyl, methoxy, methylthio, trifluoromethyl, trifluoromethoxy, trifluoromethylthio, dimethylamino, methoxycarbonyl and ethoxycarbonyl);
n is 0, 1 or 2;
Z represents a fluorine, chlorine or bromine atom or a methyl, tert.-butyl, cyclohexyl, methoxy, methylthio, trifluoromethyl, trifluoromethoxy or trifluoromethylthio group or a phenoxy, benzyl, benzyloxy or phenyl group which is optionally substituted by fluorine, chlorine and methyl;
A, B and m have the abovementioned meanings.

Further particularly preferred compounds of the present invention are those
in which
R represents a tert.-butyl, isopropyl or methyl group, represents a cyclopropyl, cyclopentyl or cyclohexyl group, each of which is optionally substituted by methyl or ethyl or represents a phenyl group which is optionally substituted by fluorine, chlorine, methyl or trifluoromethyl;
B represents sulphur;
Z represents a fluorine, chlorine or bromine atom, a methyl, tert.-butyl, cyclohexyl, methoxy, methylthio, trifluoromethyl, trifluoromethoxy or trifluoromethylthio group, or a phenoxy, benzyl, benzyloxy or phenyl group which is optionally substituted by fluorine, chlorine and methyl; and
A and m have the abovementioned meanings.

Preferred and particularly preferred compounds according to the invention, of course, include addition products of acids and those substituted 1-hydroxyalkylazolyl derivatives of the formula (I) in which the substituents A, B, R and $Z_m$ have the meanings which have already been mentioned for preferred and particularly preferred compounds of the invention.

The acids which may be used to form addition products include, as preferences, hydrohalic acids (such as hydrobromic acid and, especially, hydrochloric acid), phosphoric acid, nitric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and naphthalene-1,5-disulphonic acid).

Preferred and particularly preferred compounds according to the invention also include addition products of salts of metals of main groups II to IV and of subgroups I and II and IV to VIII and those substituted 1-hydroxyalkyl-azolyl derivatives of the formula (I) in which the substituents A, B, R and $Z_m$ have the meanings which have already been mentioned for preferred and particularly preferred compounds of the invention.

Salts of copper, zinc, manganese, magnesium, tin, iron and nickel are particularly preferred in this context. Suitable anions of these salts are those which are derived from those acids which lead to physiologically tolerated addition products. In this connection, particularly preferred acids of this type are the hydrohalic acids, (such as hydrochloric acid and hydrobromic acid) and also phosphoric acid, nitric acid and sulphuric acid.

If, for example, 2-(4-fluorophenoxymethyl)-2-(fluoro-tert.-butyl)-oxirane and 1,2,4-triazole are used as starting materials, the course of the reaction variant (a) according to the invention can be represented by the following equation:

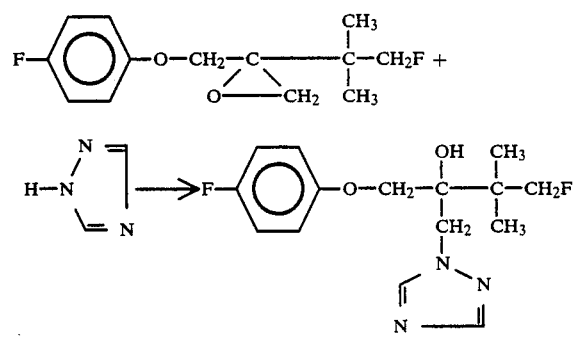

If, for example, 2-(methoxy-tert.-butyl)-2-(1,2,4-triazol-1-yl-methyl)-oxirane and 4-chlorophenol are used as starting materials, the course of the reaction variant (b) according to the invention can be represented by the following equation:

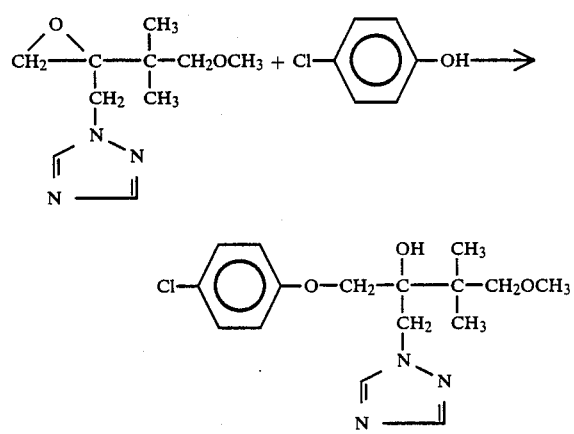

Preferred oxiranes of formula (II) to be used as starting materials in carrying out reaction variant (a) according to the invention are those in which B, R, Z and m have the meanings which have already been respectively mentioned in connection with the description of the preferred and particularly preferred compounds according to the invention.

The oxiranes of the formula (II) are novel and form a further subject of the present invention.

Oxiranes of formula (II) are interesting intermediate products, and may be obtained in a generally known manner by reacting a ketone of the general formula

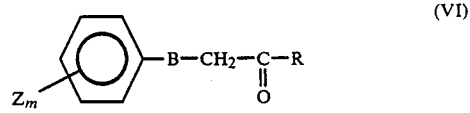

in which B, R, Z and m have the meaning given above, either (α) with dimethyloxosulphonium methylide of the formula

in the presence of a diluent, or (β) with trimethylsulphonium methylsulphate of the formula

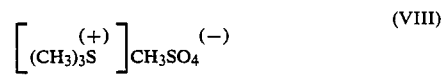

in the presence of an inert organic solvent and in the presence of a base.

The ketones of the formula (VI) which are required as starting materials in the preparation of the oxiranes of the formula (II) are known (see for example, U.S. Pat. Nos. 4,255,434; 4,154,842; 3,912,752; 4,284,639; U.S. application Ser. No. 321,642, filed Nov. 16, 1981, now pending; German Patent Specification Nos. 2,632,602, 2,635,664; 2,918,894 and 2,737,489), or they form the subject of our copending patent application Ser. Nos. 265,050, filed May 19, 1981, now pending; U.S. Ser. No. 370,754, filed Apr. 22, 1982, now pending and U.S. Ser. No. 335,942, filed Dec. 30, 1981, now pending or they may be prepared by processes which are known in principle.

The dimethyloxosulphonium methylide of the formula (VII) required in process variant (α) is likewise known (see J. Amer. Chem. Soc. 87, 1363–1364 (1965)). The above reaction is carried out using the freshly prepared starting material, by producing it in situ by reacting trimethyloxosulphonium iodide with sodium hydride or sodium amide in the presence of a diluent.

The trimethylsulphonium methylsulphate of the formula (VIII) which is required in process (β) is likewise known (see Heterocycles 8, 397 (1977)). The above reaction is also carried out using the freshly prepared starting material, by producing it in situ by reacting dimethylsulphide with dimethyl sulphate.

A preferred diluent in variant (α) of the process for the preparation of the oxiranes of the formula (II) is dimethylsulphoxide.

In the process variant (α) described above, the reaction temperatures can be varied within a relatively wide range. In general, the reaction is carried out at a temperature between 20° C. and 80° C.

The process for the preparation of the oxiranes of the formula (II) by variant (α), and the working-up of the reaction mixture obtained in this synthesis, are carried out according to customary methods (see J. Amer. Chem. Soc. 87, 1363–1364 (1965)).

A preferred inert organic solvent in variant (β) for the preparation of the oxiranes of the formula (II) is acetonitrile.

The bases used in process variant (β) may be strongly inorganic or organic bases. Sodium methylate is preferred.

In the process variant (β) described above, the reaction temperatures can be varied within a certain range. In general, the reaction is carried out at a temperature between 0° C. and 60° C., preferably at room temperature.

The process for the preparation of the oxiranes of the formula (II) by variant (β), and the working-up of the reaction product obtained in this synthesis, are carried out by customary methods (see Heterocycles 8, 397 (1977)).

In the reaction variant (a) according to the present invention, the oxiranes of the formula (II), obtained as described above, can, if required, be directly reacted further, without being isolated.

The azoles of the formula (III), additionally to be used as starting materials for reaction variant (a), are generally known compounds of organic chemistry.

Preferred azolylmethyl-oxiranes of formula (IV) to be used as starting materials in carrying out reaction variant (b) according to the invention are those in which A and R have the meanings which have already been mentioned for these substituents in connection with the description of the preferred and particularly preferred compounds according to the invention.

The azolylmethyl-oxiranes of the formula (IV) are not yet known. However, some of them form the subject of our, as yet unpublished, prior patent application corresponding to U.S. patent application Ser. No. 352,689, filed Feb. 26, 1982, now pending, or they can be obtained in a generally known manner, by epoxidizing an azolo-ketone of the general formula

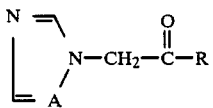

(IX)

in which A and R have the meanings given above, according to the process variants (α) and (β) given above.

The azolo-ketones of the formula (IX) are known (see U.S. application Ser. No. 792,756, filed May 2, 1977, now pending; U.S. Pat. No. 4,344,953 and DE-OS German Published Specification No. 2,638,470, or they form the subject of U.S. application Ser. No. 328,871, filed Dec. 8, 1981, now pending, or they can be prepared by processes which are known in principle.

Preferred (thio)phenols of formula (V), additionally to be used as starting materials for reaction variant (b) according to the invention, are those in which Z and m have the meanings which have already been respectively mentioned in connection with the description of the preferred and particularly preferred compounds according to the invention, and $B^1$ represents oxygen or sulphur.

The (thio)phenols of the formula (V) are generally known compounds of organic chemistry.

Suitable diluents for reaction variants (a) and (b) according to the invention are organic solvents which are inert under the reaction conditions. These include, as preferences, alcohols (such as ethanol, methoxyethanol or propanol), ketones (such as butan-2-one), nitriles (such as acetonitrile), esters (such as ethyl acetate), ethers (such as dioxane), aromatic hydrocarbons (such as benzene and toluene) or amides (such as dimethylformamide).

Suitable bases for the reactions according to the invention are any of the inorganic and organic bases which can customarily be used. These include, as preferences, alkali metal carbonates (such as sodium carbonate and potassium carbonate), alkali metal hydroxides (such as sodium hydroxide), alkali metal alcoholates (such as sodium methylate, sodium ethylate, potassium methylate and potassium ethylate), alkali metal hydrides (such as sodium hydride) and lower tertiary alkylamines, cycloalkylamines and aralkylamines (such as, especially, triethylamine).

In carrying out reaction variant (a) and (b) according to the invention, the reaction temperatures can be varied within a relatively wide range. In general, the reactions are carried out at a temperature between 0° and 200° C., preferably between 60° and 150° C.

The reactions according to the invention can, if appropriate, be carried out under elevated pressure. In general, the reaction is carried out under between 1 and 50 bar, preferably between 1 and 25 bar.

In carrying out reaction variant (a) according to the invention, 1 to 2 mols of the azole and, if appropriate, 1 to 2 mols of the base are preferably employed per mol of the oxirane of the formula (II); in carrying out reaction variant (b) according to the invention, 1 to 2 mols of the (thio)phenol of the formula (V) and, if appropriate, 1 to 2 mols of the base are preferably employed per mol of the azolylmethyl-oxirane of the formula (IV). The end products are isolated in each case in a generally known manner.

The compounds of the formula (I) which are obtainable by the processes according to the invention can be converted into acid addition salts or metal salt complexes.

The following acids are preferred for the preparation of physiologically tolerated acid addition salts of the compounds of the formula (I): hydrohalic acids (such as hydrobromic acid, and, especially, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and naphthalene-1,5-disulphonic acid).

The acid addition salts of the compounds of the formula (I) may be obtained in a simple manner by customary salt formation methods, for example by dissolving a compound of the formula (I) in a suitable inert solvent, and adding the acid, for example hydrochloric acid, and may be isolated in a known manner, for example by filtration, and purified, if appropriate, by washing with an inert organic solvent.

Preferred salts for the preparation of the metal salt complexes of the compounds of the formula (I) are salts of metals of main groups II to IV and sub-groups I and II and IV to VIII of the periodic table, copper, tin, iron and nickel being mentioned as examples.

Suitable anions of the salts are those which are preferably derived from the following acids: hydrohalic acids (such as, hydrochloric acid and hydrobromic acid), and also phosphoric acid, nitric acid and sulphuric acid.

The metal complexes of compounds of the formula (I) may be obtained in a simple manner by customary processes, thus, for example, by dissolving the metal salt in an alcohol, (for example ethanol), and adding the solution to the compound of the formula (I). Metal salt complexes may be purified in a known manner, for example by filtration, isolation and, if appropriate, by recrystallization.

The active compounds which can be used according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soy beans and cereals. Using growth regulators it is also possible, for example, to inhibit the degradation of desired constituents, such as, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds which can be employed according to the invention can be used with particularly good success for combating those fungi which cause powdery mildew diseases; thus, for combating Erysiphe species, for example against the powdery mildew of barley or of cereals causative organism (*Erysiphe graminis*) or Sphaerotheca species, for example against the powdery mildew of cucumber causative organism (*Sphaerotheca fuligenea*); and also for combating Venturia species, for example, against the apple scab causative organism (*Venturia inaequalis*); *Pellicularia sasakii* in rice, and *Pyrenophora teres* in cereals.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use suspensions, wettable powders, pastes, soluble powders, dusting agents and granules. They are used in the customary manner, for example by watering, spraying, atomizing, scattering, dusting, foaming and coating. Furthermore, it is possible to apply the active compounds in accordance with the ultra-low volume process or to inject the active compound preparation or the active compound itself into the soil. It is also possible to treat the seeds of plants.

When the compounds according to the invention are employed as plant growth regulators, the amounts applied can be varied within a substantial range. In general, 0.01 to 50 kg, preferably 0.05 to 10 kg, of the active compound are employed per hectare of soil surface.

When the substances according to the invention are employed as fungicides, also, the amount applied can be varied within a substantial range, depending on the type of application.

Thus, especially in the treatment of parts of plants, the active compound concentrations in the use forms are in general between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are generally required at the place of action.

The present invention also provides plant growth regulating or fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

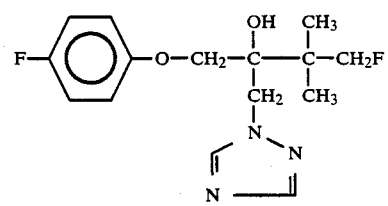
(1)

(Reaction variant (a))

15.2 g (0.22 mol) of 1,2,4-triazole were added to 0.46 g (0.02 mol) of sodium in 200 ml of n-propanol. The solution was heated to the boil, and 48.5 g (0.2 mol) of 2-(4-fluorophenoxymethyl)-2-(fluoro-tert.-butyl)-oxirane, dissolved in 50 ml of n-propanol, were added dropwise. The reaction solution was stirred under reflux for a further 48 hours and was concentrated, and 200 ml of ethyl acetate and 100 ml of water were added to the residue. The organic phase was separated off, washed twice with water, dried over sodium sulphate and concentrated. The residue was dissolved in ether, and the solution was gassed with hydrogen chloride. The precipitate formed was filtered off under suction and washed with ether, and ethyl acetate/1N sodium hydroxide solution were added. The crude product obtained was purified over a silica gel column (mobile phase: methylene chloride/ethyl acetate, 2:1), and recrystallised from acetonitrile. 17.9 g (29% of theory) of 4-fluoro-2-(4-fluorophenoxymethyl)-3,3-dimethyl-1-(1,2,4-triazol-1-yl)-butan-2-ol of melting point 97° to 99° C. were obtained.

Preparation of the Starting Material

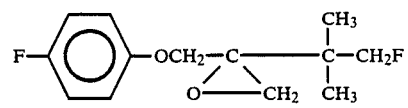

A solution of 40.5 ml (0.55 mol) of dimethyl sulphide in 50 ml of absolute acetonitrile was added to a solution of 47.3 ml (0.5 mol) of dimethyl sulphate in 250 ml of absolute acetonitrile at room temperature. The reaction mixture was stirred for 4 days at room temperature. Thereafter, 55.1 g (0.24 mol) of 4-fluoro-1-(4-chlorophenoxy)-3,3-dimethylbutan-2-one in 50 ml of absolute acetonitrile were added dropwise, and then 30.4 g (0.56 mol) of sodium methylate were added. The reaction mixture was stirred for a further 4 days. It was then concentrated, the residue was partitioned between water and ethyl acetate, the organic phase was separated off, washed twice with water and once with saturated sodium chloride solution, dried over sodium sulphate and concentrated, and the residue was distilled in vacuo. 49.1 g (85% of theory) of 2-(4-fluorophenoxymethyl)-2-(fluoro-tert.-butyl)-oxirane of boiling point 81° to 83° C./0.09 mbar were obtained.

EXAMPLE 2

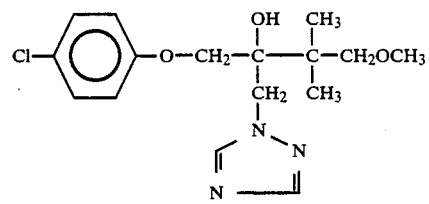
(2)

(Reaction variant (b))

8.1 g (0.0633 mol) of 4-chlorophenol were added to a solution of 0.32 g (0.014 mol) of sodium in 100 ml of absolute ethanol. 10.3 g (0.0488 mol) of 2-(methoxy-tert.-butyl)-2-(1,2,4-triazol-1-yl-methyl)-oxirane, dissolved in 300 ml of absolute ethanol, were added, and the reaction mixture was heated under reflux for 48 hours. The reaction mixture was allowed to cool and was concentrated. The residue was taken up in ethyl acetate, and the solution was washed once with water, once with 1N sodium hydroxide solution, again with water, thereafter with 1N hydrochloric acid and 1N sodium hydroxide solution, again with water, and finally with saturated sodium chloride solution. The organic phase was dried over sodium sulphate, and concentrated. 10.7 g (64.6% of theory) of 2-(4-chlorophenoxymethyl)-3,3-dimethyl-4-methoxy-1-(1,2,4-triazol-1-yl)-butan-2-ol of refractive index $n_D^{20} = 1.531$ were obtained.

Preparation of the Starting Material

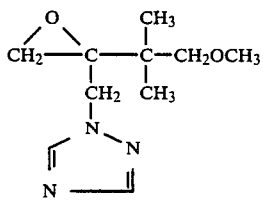

24 g (1 mol) of sodium hydride (80% strength in paraffin oil) and 220 g (1 mol) of trimethylsulphoxonium iodide were mixed under a nitrogen atmosphere at 10° C., and 1,000 ml of dimethylsulphoxide were added slowly. After one hour, 177.5 g (0.9 mol) of 3,3-dimethyl-4-methoxy-1-(1,2,4-triazol-1-yl)-butan-2-one, dissolved in 200 ml of tetrahydrofuran, were added dropwise to the suspension.

The mixture was stirred for 2 days at room temperature. The solvent was stripped off in a high vacuum, and the residue was stirred with ethyl acetate and filtered under suction. The filtrate was washed three times with dilute sodium chloride solution, dried over sodium sulphate and concentrated, and the residue was distilled in a high vacuum. 163 g (86% of theory) of 2-(methoxy-tert.-butyl)-2-(1,2,4-triazol-1-yl-methyl)-oxirane of boiling point 89° to 92° C./0.008 mbar were obtained.

EXAMPLE 3

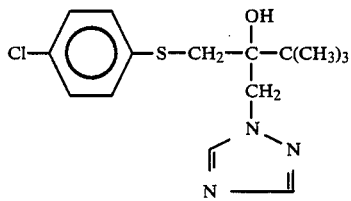

(Reaction variant (b))

5.4 g (0.1 mol) of sodium methylate were introduced in portions into a mixture of 18 g (0.1 mol) of 2-tert.-butyl-2-(1,2,4-triazol-1-yl-methyl)-oxirane and 14.5 g (0.1 mol) of 4-chlorothiophenol in 250 ml of acetonitrile. The mixture was stirred under reflux for 16 hours, and concentrated in vacuo. The residue was dissolved in chloroform, and the solution was washed with water, dried over sodium sulphate, filtered and concentrated. The residual oil was chromatographed over a silica gel column. 6.9 g (21% of theory) of 2-(4-chlorophenylthiomethyl)-3,3-dimethyl-1-)1,2,4-triazol-1-yl)-butan-2-ol of melting point 54° to 55° C. were obtained.

Preparation of the Starting Material

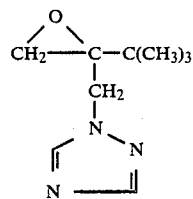

6 g (0.11 mol) of sodium methylate were introduced in portions into a suspension of 24 g (0.11 mol) of trimethylsulphoxonium iodide in 24 g of dimethylsulphoxide.

10 ml of tetrahydrofuran were also added, and the reaction mixture was then stirred for 5 hours at room temperature. Thereafter, a solution of 16.8 g (0.1 mol) of 1,2,4-triazol-1-yl-pinacolin in 100 ml of tetrahydrofuran was added dropwise, and the mixture was heated at 70° C. for 5 hours. The reaction mixture was filtered, and the filtrate was concentrated in vacuo. The residue was dissolved in chloroform, and the solution was washed with water, dried over sodium sulphate, filtered and concentrated. 13.8 g of a 69.4% pure 2-tert.-butyl-2-(1,2,4-triazol-1-yl-methyl)-oxirane of refractive index $n_D^{20} = 1.4872$ were obtained.

EXAMPLE 4

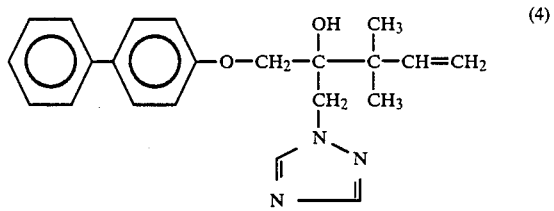

(4)

(Reaction variant (a))

35.3 g (0.120 mol) of 2-(biphenyl-4-yloxymethyl)-2-(3,3-dimethylprop-1-en-3-yl)-oxirane, dissolved in 80 ml of n-propanol, were added to a boiling solution of 1 g (0.012 mol) of sodium propylate and 9.1 g (0.132 mol) of 1,2,4-triazole in 50 ml of n-propanol. After the solution had been boiled under reflux for two days, it was evaporated down under reduced pressure, the oily residue was taken up in 200 ml of ethyl acetate, and the solution was washed with three times 50 ml of water. After the organic phase had been dried over anhydrous sodium sulphate, the solution was concentrated under reduced pressure. After the residue had been triturated with 150 ml of ethyl acetate,, 6.6 g (15.1% of theory) of 4-(biphenyl-4-yloxymethyl)-3,3-dimethyl-4-hydroxy-5-(1,2,4-triazol-4-yl)-pent-1-ene were obtained as colorless crystals of melting point 171° to 173° C. The oil (37.1 g) which remained after the filtrate had been evaporated down was taken up in 200 ml of acetone, and a solution of 34.6 g of naphthalene-1,5-disulphonic acid in 100 ml of acetone was added. The salt which crystallized out was filtered off under suction, washed with acetone, and taken up in a mixture of 250 ml of water and 250 ml of dichloromethane. The solution was rendered alkaline by stirring in 10% strength sodium carbonate solution. After the organic phase had been concentrated, 24 g of an oil were obtained, which was dissolved in ethyl acetate and the solution then filtered over silica gel. After the filtrate had been concentrated, 17.8 g (40.8% of theory) of 4-(biphenyl-4-yloxymethyl)-3,3-dimethyl-4-hydroxy-5-(1,2,4-triazol-1-yl)-pent-1-ene were obtained in the form of colorless crystals of melting point 85° to 87° C.

Preparation of the Starting Material

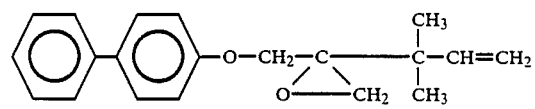

A solution of 41.9 ml (0.567 mol) of dimethyl sulphide in 50 ml of acetonitrile was added dropwise to a solution of 49.4 ml (0.518 mol) of dimethyl sulphate in 250 ml of acetonitrile at 25° C., in the course of 2 hours, with external cooling. After the mixture had stood for 4 days at room temperature, 87.4 g (0.31 mol) of 5-(biphenyl-4-yloxy)-3,3-dimethylpent-1-en-4-one, dissolved in 90 ml of acetonitrile, were stirred in in the course of 1 hour. Thereafter, 31.6 g (0.58 mol) of sodium methylate were introduced at 25° C. After the mixture had been stirred for twelve hours at room temperature, the precipitated salt was filtered off, and the filtrate was concentrated. The oily residue was taken up in 500 ml of ethyl acetate, and the solution was washed with twice 500 ml of water and dried over anhydrous sodium sulphate. After the solution had been concentrated in vacuo, 73.4 g (80.4% of theory) of 2-(biphenyl-4-yloxymethyl)-2-(3,3-dimethylprop-1-en-3-yl)-oxirane were obtained as a colorless waxy mass.

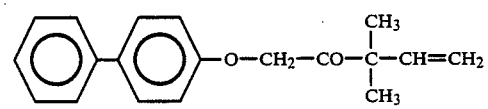

196.5 g (1.34 mol) of 5-chloro-3,3-dimethylpent-1-en-4-one were added dropwise to a mixture of 184.9 g (1.34 mol) of potassium carbonate and 227.8 g (1.34 mol) of 4-hydroxybiphenyl in 1,000 ml of boiling acetone, in the course of one hour. The mixture was heated to the boil after 5 hours, allowed to cool to room temperature, and filtered off from the precipitated potassium chloride. The oil which remained after the filtrate had been concentrated was taken up in 1,000 ml of ethyl acetate. The solution was washed twice with 150 ml each of 10% strength sodium carbonate solution and water, and dried over anhydrous sodium sulphate, and the solvent was distilled off. Residual amounts of solvent were stripped off at 0.13 mbar (bath temperature: 180° C.). 357.2 (95% of theory) of 5-(biphenyl-4-yloxy)-3,3-dimethylpent-1-en-4-one of melting point 42° to 44° C. were obtained in this manner.

EXAMPLE 5

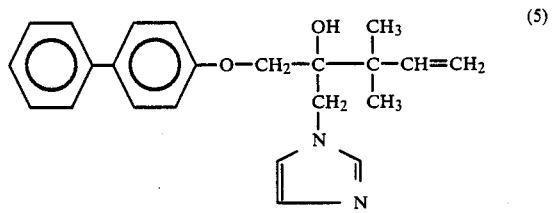

(Reaction variant (a))

35.3 g (0.120 mol) of 2-(biphenyl-4-yloxymethyl)-2-(3,3-dimethylprop-1-en-3-yl)-oxirane, dissolved in 80 ml of n-propanol, were added to a boiling solution of 1 g (0.012 mol) of sodium propylate and 9 g (0.132 mol) of imidazole in 50 ml of n-propanol, in the course of 5 minutes. After the solution had been boiled under reflux for two days, the solvent was distilled off under reduced pressure, the residue was taken up in a mixture of 150 ml of ethyl acetate and 100 ml of dichloromethane, and the solution was washed with three times 50 ml of water. After the organic phase had been dried over anhydrous sodium sulphate, the solution was concentrated to dryness under reduced pressure. 10 ml of ethyl acetate were added to the solid residue, and the product was filtered off. 27.2 g (62.5% of theory) of 4-(biphenyl-4-yloxymethyl)-3,3-dimethyl-4-hydroxy-5-(imidazol-1-yl)pent-1-ene were obtained in the form of colorless crystals of melting point 151° to 153° C. in this manner.

The compounds below, of the general formula

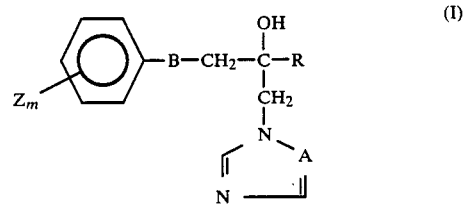

were obtained in an analogous manner and according to reaction variants (a) and (b) according to the invention:

| Example No. | $Z_m$ | B | A | R | Melting point (°C.) or refractive index $n_D^{20}$ |
| --- | --- | --- | --- | --- | --- |
| 6 | 4-CH$_3$ | O | N | —C(CH$_3$)$_2$CH$_2$F | 91–92 |
| 7 | 4-Cl | O | N | —C(CH$_3$)$_2$CH$_2$F | 111–13 |
| 8 | 4-Cl,2-CH$_3$ | O | N | —C(CH$_3$)$_2$CH$_2$F | 119–20 |
| 9 | 2,4-Cl$_2$ | O | N | —C(CH$_3$)$_2$CH$_2$F | 107–09 |
| 10 | 4-Cl | S | N | —C(CH$_3$)$_2$CH$_2$F | 87 |
| 11 | 2-Cl | S | N | —C(CH$_3$)$_2$CH$_2$F | 1.552 |
| 12 | 3,4-Cl$_2$ | S | N | —C(CH$_3$)$_2$CH$_2$F | 1.5710 |
| 13 | 4-Cl | O | N | —C(CH$_2$F)$_2$CH$_3$ | 111–12 |
| 14 | 2,4-Cl$_2$ | O | N | —C(CH$_2$F)$_2$CH$_3$ | 109–10 |
| 15 | 4-Cl,2-CH$_3$ | O | N | —C(CH$_2$F)$_2$CH$_3$ | 138–39 |
| 16 | 2,4-Cl$_2$ | O | N | —C(CH$_3$)$_2$CH$_2$OCH$_3$ | 49–55 |
| 17 | 4-Cl, 2-CH$_3$ | O | N | —C(CH$_3$)$_2$CH$_2$OCH$_3$ | 1.537 |
| 18 | 4-Cl | O | N | —C(CH$_3$)$_2$CH$_2$OC$_2$H$_5$ | 69–73 |
| 19 | 4-Cl | O | N | 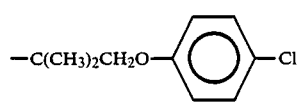 | 125–26 |
| 20 | 4-F | O | N | —C(CH$_3$)$_2$CH$_2$OCH$_3$ | 1.5152 |

-continued

| Example No. | $Z_m$ | B | A | R | Melting point (°C.) or refractive index $n_D^{20}$ |
|---|---|---|---|---|---|
| 21 | 2,4-Cl$_2$ | O | N | —C(CH$_3$)$_2$—C$_6$H$_4$—Cl | 1.5805 |
| 22 | 4-Cl | O | N | —C(CH$_3$)$_2$—CH=CH$_2$ | 58–59 |
| 23 | 2,4-Cl$_2$ | O | N | —C(CH$_3$)$_2$—CH=CH$_2$ | 86–87 |
| 24 | 4-F | O | N | —C(CH$_3$)$_2$—CH=CH$_2$ | 66–68 |
| 25 | 4-Cl | CH$_2$ | N | —C(CH$_3$)$_2$CH$_2$F | 110–12 |
| 26 | 2,4-Cl$_2$ | CH$_2$ | N | —C(CH$_3$)$_2$CH$_2$F | 88–90 |
| 27 | 2,4-Cl$_2$ | CH$_2$ | N | —C(CH$_2$F)$_2$CH$_3$ | 97–99 |
| 28 | 4-Cl | CH$_2$ | N | —C(CH$_2$F)$_2$CH$_3$ | 122–24 |
| 29 | 4-Cl | CH$_2$ | N | —C(CH$_3$)$_2$CH$_2$O—C$_6$H$_4$—Cl | 120–21 |
| 30 | 4-Cl | CH$_2$ | N | —C(CH$_3$)$_2$O—C$_6$H$_3$(Cl)—Cl | 116–18 |
| 31 | 4-Cl | O | CH | —C(CH$_2$F)$_2$CH$_3$ | 165–67 |
| 32 | 2,4-Cl$_2$ | O | CH | —C(CH$_2$F)$_2$CH$_3$ | 148–50 |
| 33 | 4-Cl, 2-CH$_3$ | O | CH | —C(CH$_2$F)$_2$CH$_3$ | 133–35 |
| 34 | 4-Cl | CH$_2$ | CH | —C(CH$_3$)$_2$O—C$_6$H$_4$—Cl | 118–20 |
| 35 | 4-Cl | CH$_2$ | CH | —C(CH$_3$)$_2$CH$_2$O—C$_6$H$_3$(Cl)—Cl | 121–23 |
| 36 | 2,4-Cl$_2$ | CH$_2$ | CH | —C(CH$_2$F)$_2$CH$_3$ | 96–99 |
| 37 | 4-Cl | CH$_2$ | CH | —C(CH$_2$F)$_2$CH$_3$ | 128–37 |
| 38 | 2,4-Cl$_2$ | CH$_2$ | CH | —C(CH$_3$)$_2$CH$_2$F | 103–06 |
| 39 | 2,4-Cl$_2$ | O | CH | —C(CH$_3$)$_2$—CH=CH$_2$ | 136–37 |
| 40 | 4-F | O | CH | —C(CH$_3$)$_2$—CH=CH$_2$ | 135–36 |
| 41 | 3,4-Cl$_2$ | S | N | —C(CH$_3$)$_3$ | 97 |
| 42 | 4-OCF$_3$ | O | N | —C(CH$_3$)$_2$CH$_2$OCH$_3$ | 1,4882 |
| 43 | 4-OCF$_3$ | O | N | —C(CH$_3$)$_2$CH$_2$OC$_2$H$_5$ | 1,4836 |
| 44 | 4-Cl | O | N | —C(CH$_3$)$_2$—O—C$_6$H$_4$—Cl | resin |
| 45 | 4-F | O | N | —C(CH$_3$)$_2$—O—C$_6$H$_4$—Cl | " |
| 46 | 2,4-Cl$_2$ | O | N | —C(CH$_3$)$_2$—O—C$_6$H$_4$—Cl | " |
| 47 | 4-C$_6$H$_5$ | O | N | —C(CH$_3$)$_2$—O—C$_6$H$_4$—Cl | " |

-continued

| Example No. | $Z_m$ | B | A | R | Melting point (°C.) or refractive index $n_D^{20}$ |
|---|---|---|---|---|---|
| 48 | 4-Cl | O | N | 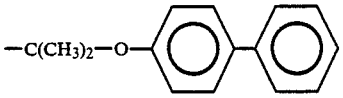 | " |
| 49 | 2,4-Cl$_2$ | O | N | 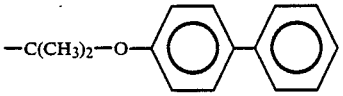 | " |
| 50 | 2,4-Cl$_2$ | O | N | 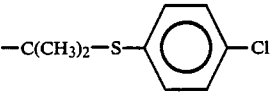 | 115 |
| 51 | 4-Cl | O | N | 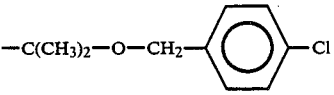 | 133 |
| 52 | 2,4-Cl$_2$ | O | N | 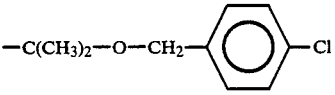 | 102 |

The fungicidal and plant gorwth regulating activity of the compounds of this invention is illustrated by the following biotest examples.

In there examples, the compounds according to the present invention are each identified by the number (given in brackets) of the corresponding preparative example.

The known comparison compounds are identified as follows:

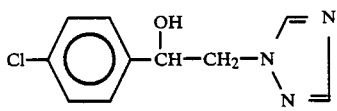 (A)

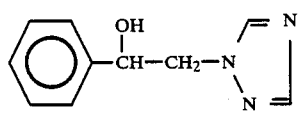 (B)

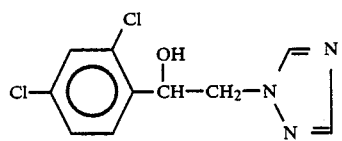 (C)

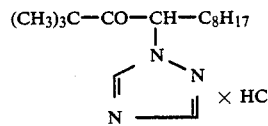 (D)

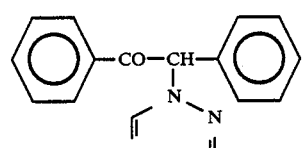 (E)

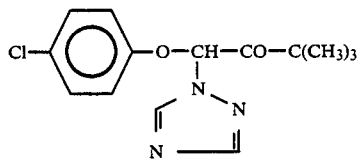 (F)

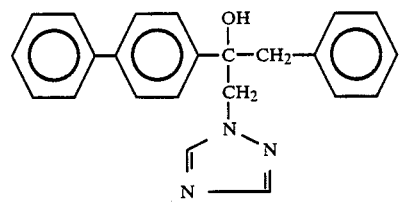 (G)

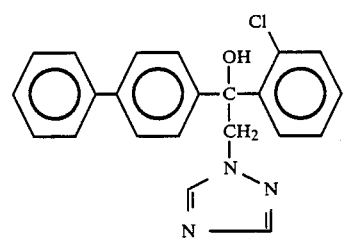 (H)

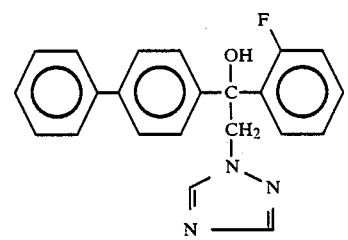 (I)

EXAMPLE A

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f.sp.hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared to the prior art was shown, for example, by the compounds (15), (14), (13), (19), (18), (17), (16), (2), (9), (8), (7), (6), (1), (32), (33), (21) and (11).

EXAMPLE B

Erysiphe test (barley)/seed treatment.

The active compounds were used as dry dressings. These were prepared by extending the particular active compound with a ground mineral to give a finely pulverulent mixture, which ensured uniform distribution on the seed surface.

To apply the dressing, the seed was shaken with the dressing in a closed glass flask for 3 minutes.

3 batches of 12 grains of the barley were sown 2 cm deep in standard soil. 7 days after sowing, when the young plants had unfolded their first leaf, they were dusted with spores of Erysiphe graminis f.sp.hordei.

The plants were placed in a greenhouse at a temperature of about 20° C. and a relative atmospheric humidity of about 80% in order to promote the development of powdery mildew pustules.

Evaluation was carried out 7 days after the inoculation.

In this test, a clearly superior activity compared with the prior art is shown, for example, by the compounds (15), (14), (13), (18), (17), (16), (7), (6) and (1).

EXAMPLE C

Venturia test (apple)/protective
Solvent: 4.7 parts by weight of acetone
Emulsifier: 0.3 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated with an aqueous conidia suspension of the apple scab causative organism (Venturia inaequalis) and then remained in an incubation cabinet at 20° C. and 100% relative atmospheric humidity for 1 day.

The plants were then placed in a greenhouse at 20° C. and a relative atmospheric humidity of about 70%.

Evaluation was carried out 12 days after the inoculation.

In this test, a clearly superior activity compared with the prior art was shown, for example, by the compounds (18), (17), (16), (9), (8) and (7).

EXAMPLE D

Sphaerotheca test (cucumber)/protective
Solvent: 4.7 parts by weight of acetone
Emulsifier: 0.3 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were dusted with conidia of the fungus Sphaerotheca fuliginea.

The plants were than placed in a greenhouse at 23° to 24° C. and at a relative atmospheric humidity of about 75%.

Evaluation was carried out 10 days after the inoculation.

In this test, a clearly superior activity compared with the prior art was shown, for example, by the compounds (17), (16), (2), (9), (8), (7), (6), (1) and (21).

EXAMPLE E

Pellicularia test (rice)
Solvent: 12.5 parts by weight of acetone
Emulsifier: 0.3 part by weight of alkylaryl polyglycol ether To produce a suitable preparation of active compound, 1 part by weight of active compound was mixed with the stated amount of solvent, and the concentrate was diluted with water and the stated amount of emulsifier, to the desired concentration.

To test for activity, young rice plants in the 3 to 4 leaf stage were sprayed until dripping wet. The plants remained in a greenhouse until they had dried off. The plants were then inoculated with Pellicularia sasakii and were placed at 25° C. and 100% relative atmospheric humidity.

The evaluation of the disease infestation was carried out 5 to 8 days after the inoculation.

In this test, a clearly superior activity compared with the prior art was shown, for example, by the compounds (6), (7), (8) and (9).

EXAMPLE F

Inhibition of Growth of Cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth of the plants was measured and the inhibition of growth in per cent of the additional growth of the control plants was calculated. 100% inhibition of growth meant that growth had stopped and 0% denoted a growth corresponding to that of the control plants.

In this test, the active compounds (1), (6), (7), (8), (13), (17) and (16) according to the invention showed a better inhibition of growth than the compounds (B), (C), (H) and (I) known from the prior art.

EXAMPLE G

Inhibition of Growth of Soy Beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soy bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in per cent of the additional growth of the control plants was calculated. 100% inhibition of growth meant that growth had stopped and 0% denoted a growth corresponding to that of the control plants.

In this test, the active compounds, (1), (6), (7), (8), (9), (2), (14) and (13) according to the invention showed a better inhibition of growth than the compounds (B), (C) and (H) known from the prior art.

EXAMPLE H

Influence on Growth of Sugar Beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparation of active compound until dripping wet. After 14 days, the additional growth of the plants was measured and the influence on growth in per cent of the additional growth of the control plants was calculated. 0% influence on growth denoted a growth which corresponds to that of the control plants. Negative values characterized an inhibition of growth in comparison to the control plants, while positive values characterized a promotion of growth in comparison to the control plants.

In this test, the active compounds (21), (1), (6), (7), (8), (2), (17) and (16) according to the invention had a greater influence on growth than the compounds (A), (H) and (I) known from the prior art.

It will be understood that the specification and examples are illustrative but not limitative of the present invention and that other embodiments within the spirit and scope of the invention will suggest themselves to those skilled in the art.

We claim:

1. A substituted 1-hydroxyalkylazolyl derivative of the formula

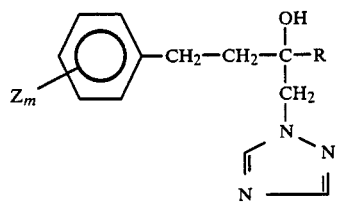

in which
R is

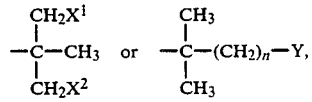

$X^1$ is a hydrogen, fluorine or chlorine atom,
$X^2$ is a fluorine or chlorine atom,
Y is methoxy, ethoxy, methylthio, ethylthio, isopropylthio, or phenyl, phenoxy or phenylthio wherein the phenyl group is optionally substituted by one or two substituents selected from the group consisting of fluorine, chlorine and methyl,
n is 0, 1 or 2,
Z is fluorine, chlorine, methyl, phenyl or chlorophenyl, and
m is 0, 1 or 2,
or an addition product thereof with an acid or metal salt.

2. A compound according to claim 1 wherein such compound is 4-(2,4-dichlorophenoxy)-1-(4-chlorophenyl)-3-(1,2,4-triazolyl-methyl)-4-methyl-pentan-3-ol of the formula

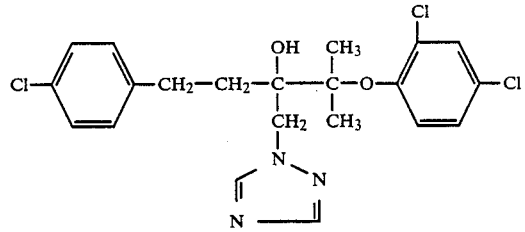

or an addition product thereof with an acid or metal salt.

3. A fungicidal or plant-growth regulating composition, comprising a fungicidally or plant-growth regulating effective amount of a compound or addition product thereof according to claim 1 in admixture with an inert diluent.

4. A method of combating fungi comprising applying to the fungi, or to a habitat thereof, a fungicidally effective amount of a compound or addition product thereof according to claim 1.

5. A method of regulating the growth of plants comprising applying to the plants, or to a habitat thereof, a plant-growth regulating effective amount of a compound or addition product thereof according to claim 1.

6. The method according to claim 1 wherein such compound is 4-(2,4-dichlorophenoxy)-1-(4-chlorophenyl)-3-(1,2,4-triazolyl-methyl)-4-methyl-pentan-3-ol,
or an addition product thereof with an acid or metal salt.

* * * * *